United States Patent [19]
Au-Young et al.

[11] Patent Number: 5,840,866
[45] Date of Patent: Nov. 24, 1998

[54] HUMAN UBIQUITIN-CONJUGATING ENZYME

[75] Inventors: Janice Au-Young, Berkeley; Surya K. Goli, Sunnyvale; Jennifer L. Hillman, San Jose, all of Calif.

[73] Assignee: Incyte Pharmaceuticals, Inc., Palo Alto, Calif.

[21] Appl. No.: 679,765

[22] Filed: Jul. 10, 1996

[51] Int. Cl.[6] .............................. C07H 21/04; C12N 9/10; C12N 1/20; C12N 15/00
[52] U.S. Cl. ................... 536/23.2; 435/193; 435/252.3; 435/252.33; 435/320.1; 536/23.5
[58] Field of Search ........................... 435/193, 252.33, 435/320.1, 69.1; 536/23.2, 23.5

[56] References Cited

U.S. PATENT DOCUMENTS 5,650,313   7/1997   Ni et al. .................................. 435/193

OTHER PUBLICATIONS

Finley, et al., "Ubiquitination", *Annu.Rev.Cell Biol.* (1991) 7:25–69.

Scheffner, et al., "Protein ubiquitination involving an E1–E2–E3 enzyme ubiquitin thioester cascade", *Nature* (1995) 81–83.

Nuber, U. et al., "Cloning of Human Ubiquitin–conjugating Enzymes UbcH6 and UbcH7 (E2–F1) and Characterization of Their Interaction with E6–AP and RSP5", *J.Biol.Chem.* (1996) 271:2795–2800.

Prendergast, J.A. et al., "Increased Ubiquitin Expression Suppresses the Cell Cycle Defect Associated with the Yeast Ubiquitin Conjugating Enzyme, CDC34 (UBC3)", *J.Biol.Chem.* (1995) 270:9347–9352.

Liu, Y. et al., "Intragenic Suppression among CDC34 (UBC3) Mutations Defines a Class of Ubiquitin–Conjugating Catalytic Domains", *Mol.Cell.Bio.* (1995) 15:5635–5644.

Banerjee A. et al., "Characterization of a Dominant Negative Mutant of the Cell Cycle Ubiquitin–conjugating Enzyme Cdc34", *J.Biol.Chem.* (1995) 270:26209–26215.

Llovera, M. et al., "Muscle Wasting Associated with Cancer Cachexia is Linked to an Important Activation of the ATP–Dependent Ubiquitin–Mediated Proteolysis", *Int.J.Cancer* (1995) 61:138–141.

Attaix, D. et al., "Regulation of ATP–ubiquitin–dependent proteolysis in muscle wasting", *Reprod.Nutr.Dev.* (1994) 34:583–597.

Voisin, L. et al., "Muscle Wasting in a Rat Model of Long–lasting Sepsis Results from the Activation of Lysosomal $Ca^{2+}$–activated, and Ubiquitin–Proteasome Proteolytic Pathways", *J.Clin.Invest.* (1996) 97:1610–1617.

Gregori, L. et al., "Ubiquitin–Mediated Degradative Pathway Degrades the Extracellular but Not the Intracellular Form of Amyloid β–Protein Precursor", *Biochem.Biophys.Res.Comm.* (1994) 203:1731–1738.

Morishima, M. et al., "Posttranslational Modifications of Tau in Paired Helical Filaments", *Dementia* (1994) 5:282–288.

Grant, E.P. et al., "Rate of Antigen Degradation by the Ubiquitin–Proteasome Pathway Influences MHC Class I Presentation", *J.Immun.* (1995) 155:3750–3758.

Gosink, M.M. et al., "Redirecting the specificity of ubiquitination by modifying ubiquitin–conjugating enzymes", *Proc.Natl.Acad.Sci.USA* (1995) 92:9117–9121.

Barrell, B. et al. (Direct Submission), GenBank Sequence Database (Accession 798905), National Center for Biotechnology Information, National Library of Medicine, Bethesda, Maryland, 20894.

Seufer, W. et al., "Ubiquitin–conjugating enzymes UBC4 and UBC5 mediate selective degradation of short–lived and abnormal proteins", *EMBO J*, (1990) 9(2), 543–550 (Accession X17493).

*Primary Examiner*—Rebecca E. Prouty
*Assistant Examiner*—Elizabeth Slobodyansky
*Attorney, Agent, or Firm*—Lucy J. Billings; Incyte Pharmaceuticals, Inc.

[57] ABSTRACT

The present invention provides a polynucleotide (ubcp) which identifies and encodes a novel ubiquitin-conjugating enzyme (UBCP). The invention provides for genetically engineered expression vectors and host cells comprising the nucleic acid sequence encoding UBCP. The invention also provides for the use of substantially purified UBCP and its agonists, antagonists, or inhibitors in the commercial production of recombinant proteins and in pharmaceutical compositions for the treatment of diseases associated with the expression of UBCP. Additionally, the invention provides for the use of antisense molecules to ubcp in pharmaceutical compositions for treatment of diseases associated with the expression of UBCP. The invention also describes diagnostic assays which utilize diagnostic compositions comprising the polynucleotide, fragments or the complement thereof, which hybridize with the genomic sequence or the transcript of ubcp or anti-UBCP antibodies which specifically bind to UBCP.

4 Claims, 8 Drawing Sheets

```
5' CTC CCG GAG GTG GTG GCT TCA CTT TCC AGG ACT CAG GGG CAG CCA CAG CGA CAG          54
         9          18          27          36          45

CCG CGG GCA GCC TCA GGA GCC GGA ACG GCC GGG GGC GGC AGC                         108
         63          72          81          90          99

GGC GGC GCT GAG GGA TCT AAA ATG TCC ACT GAG GCA CAA AGA GTT GAT GAC AGT         162
         117         126         135         144         153
                              M   S   T   E   A   Q   R   V   D   D   S

CCA AGC ACT AGT GGA AGT TCC GAT GGA GAT CAA CGT GAA AGT GTT CAG CAA            216
         171         180         189         198         207
     P   S   T   S   G   S   S   D   G   D   Q   R   E   S   V   Q   Q

GAA CCA GAA AGA GAA CAA GTT CAG CCC AAG AAA GAG GGA AAA ATA TCC AGC            270
         225         234         243         252         261
     E   P   E   R   E   Q   V   Q   P   K   K   E   G   K   I   S   S

AAA ACC GCT GCT AAA TTG TCA ACT AGT GCT AAA AGA ATT CAG AAG GAA CTT GCA        324
         279         288         297         306         315
     K   T   A   A   K   L   S   T   S   A   K   R   I   Q   K   E   L   A

GAA ATC ACA TTG GAC CCT CCT CCC AAC TGT AGT GCT GGA CCC AAA GGA GAC AAC        378
         333         342         351         360         369
     E   I   T   L   D   P   P   P   N   C   S   A   G   P   K   G   D   N
```

FIGURE 1A

```
     387            396            405            414            423            432
ATT TAT GAA TGG AGG TCA ACT ATA TTG GGA CCC CCA GGA TCT GTC TAT GAA GGA
 I   Y   E   W   R   S   T   I   L   G   P   P   G   S   V   Y   E   G
     441            450            459            468            477            486
GGG GTG TTC TTT CTT GAC ATT ACC TTT TCA CCA GAC TAT CCG TTT AAA CCC CCT
 G   V   F   F   L   D   I   T   F   S   P   D   Y   P   F   K   P   P
     495            504            513            522            531            540
AAG GTT ACC TTC CGA ACA AGA ATC TAT CAC TGT AAT ATT AAC AGC CAA GGT GTG
 K   V   T   F   R   T   R   I   Y   H   C   N   I   N   S   Q   G   V
     549            558            567            576            585            594
ATC TGT CTG GAC ATC TTA AAG GAC AAC TGG AGT CCG GCT TTA ACT ATT TCT AAA
 I   C   L   D   I   L   K   D   N   W   S   P   A   L   T   I   S   K
     603            612            621            630            639            648
GTT CTC TCC ATC TGC TCA CTT ACA GAT TGN AAC CCT GAC CCT CTG
 V   L   S   I   C   S   L   T   D   X   N   P   A   D   P   L
     657            666            675            684            693            702
GTG GGC AGC ATC GCC ACA CAG TAC ATG ACC AAC AGA GCA GAG CAT GAC CGG NTG
 V   G   S   I   A   T   Q   Y   M   T   N   R   A   E   H   D   R   X
     711            720            729            738
GCC AGA CAG TGG ACC AAG CGG TAC GCC ACA TAG GGG CCT GCT GT 3'
 A   R   Q   W   T   K   R   Y   A   T
```

FIGURE 1B

The Electronic Northern for Clone: 618887
and Stringency = 50

| Library | Lib Description | Abun | Pct Abun |
|---|---|---|---|
| THP1PLB01 | THP-1 promonocyte cell line, treated PMA, LPS | 4 | 0.181 |
| COLNNOT09 | colon, 60 yr M | 2 | 0.142 |
| SCORNON01 | spinal cord, 71 M, NORM | 1 | 0.138 |
| PITUNOR01 | pituitary, 16-70 M/F, RP | 1 | 0.123 |
| RATRNOT01 | heart, right atrium, 51 F | 1 | 0.086 |
| BEPINON01 | bronchial epithelium, primary cell line, 54 M, NORM | 2 | 0.061 |
| PROSNOT05 | prostate, 67 M, match to PROSTUT03 | 1 | 0.058 |
| KIDNTUT01 | kidney tumor, Wilms, 8m F | 2 | 0.053 |
| PLACNOM03 | placenta, fetal, NORM, WM | 1 | 0.052 |
| HNT2AGT01 | hNT2 cell line, post-mitotic neurons | 2 | 0.038 |
| STOMTUT01 | stomach tumor, 52 M, match to STOMNOT02 | 1 | 0.037 |
| MMLR2DT01 | macrophages (adher PBMNC), M/F, 48-hr MLR | 2 | 0.035 |
| PROSNOT06 | prostate, 57 M, match to PROSTUT04 | 1 | 0.033 |
| MMLR3DT01 | macrophages (adher PBMNC), M/F, 72-hr MLR | 1 | 0.033 |
| TBLYNOT01 | T-B lymphoblast cell line, leukemia | 1 | 0.033 |
| BSTMNON02 | brain stem, 72 M, NORM | 1 | 0.032 |
| STOMNOT02 | stomach, 52 M, match to STOMTUT01 | 1 | 0.031 |
| BRSTTUT02 | breast tumor, 54 F, match to BRSTNOT03 | 1 | 0.030 |
| COLNNOT16 | colon, sigmoid, 62 M | 1 | 0.029 |
| TONGTUT01 | tongue tumor, carcinoma, 36 M | 1 | 0.029 |
| MELANON01 | melanocytes, M, NORM, WM | 2 | 0.025 |

FIGURE 2A

| | | |
|---|---|---|
| TMLR3DT02 | lymphocytes (non-adher PBMNC), M/F, 72-hr MLR | 1 | 0.025 |
| MMLR1DT01 | macrophages (adher PBMNC), M/F, 24-hr MLR | 1 | 0.024 |
| LUNGNOT03 | lung, 79 M, match to LUNGTUT02 | 1 | 0.020 |
| CRBLNOT01 | brain, cerebellum, 69 M | 1 | 0.019 |
| SYNORAB01 | synovium, hip, rheumatoid, 68 F | 1 | 0.019 |
| CERVNOT01 | cervix, 35 F | 1 | 0.019 |
| LUNGNOT04 | lung, 2 M | 1 | 0.018 |
| SYNOOAT01 | synovium, knee, osteoarthritis, 82 F | 1 | 0.016 |
| PGANNOT01 | brain, paraganglia, 46 M | 1 | 0.016 |
| EOSIHET02 | eosinophils, hypereosinophilia, 48 M | 1 | 0.010 |
| LIVSFEM02 | liver/spleen, fetal M, NORM, WM | 1 | 0.006 |
| PLACNOM02 | placenta, neonatal F, NORM, WM | 1 | 0.006 |

```
1    MSTEAQRVDDSPSTSGGSSDGDQRESVQQEPEREQVQPKK    SEQ ID NO 1
1    MSDDDSRASTSSSSSSN-----------QTEKETNTPKK    GI 1064914
1    MS---------------------------------GI 4718
1    MS----SRKSTASS-------------LLLRQYRELTDPKK    GI 798905

41   KEGKISKTAAKL-STSAKRIQKELAEITLDPPPNCSAGP    SEQ ID NO 1
32   KESKVSMSKNSKLLSTSAKRIQKELADITLDPPPNCSAGP    GI 1064914
3    ---------SSKRIAKELSDLERDPPTSCSAGP    GI 4718
25   ----------AIPSFHIELED---------    GI 798905

80   KGDNIYEWRSTILG-PPGSVYEGGVFFLDITFSPDYPFKP    SEQ ID NO 1
72   KGDNIYEWRSTILG-PPGSVYEGGVFFLDITFTPEYPFKP    GI 1064914
27   VGDDLYHWQASIMGPADSPYAGGVFFELSIHFPTDYPFKP    GI 4718
36   -DSNIFTWNIGVMVLNEDSIYHGGFEKAQMRFPEDFPFSP    GI 798905

119  PKVTFRTRIYHCNINSQGVICLDDILKDN----    SEQ ID NO 1
111  PKVTFRTRIYHCNINSQGVICLDDILKDN----    GI 1064914
66   PKISFTTKIYHPNINANGNICLDDILKDQ----    GI 4718
75   PQFRETPAIYHPNVYRDGRLCISILHQSGDPMTDEPDAET    GI 798905

147  WSPALTISKVLLSICSLLTDXNPADPLVGSIATQYMTNRA    SEQ ID NO 1
139  WSPALTISKVLLSICSLLTDCNPADPLVGSIATQYMTNRA    GI 1064914
94   WSPALTLSKVLLSICSLLTDANPDDPLVPEIAHIYKTDRP    GI 4718
115  WSPVQTVESVLISIVSLLEDPNINSPANVDAAVDYRKNPE    GI 798905
```

FIGURE 3A

```
187 E H D R X A R Q - - - - - - - - - - - - - - - - - - - - - - - - - - -    SEQ ID NO 1
179 E H D R M A R Q - - - - - - - - - - - - - - - - - - - - - - - - - - -    GI 1064914
134 K Y E A T A R E - - - - - - - - - - - - - - - - - - - - - - - - - - -    GI 4718
155 Q Y K Q R V K M E V E R S K Q D I P K G F I M P T S E S A Y I S Q S K L D E P E    GI 798905

195 - - - - - - - - - - - - - - - - - - - - - - - T K R Y A - - - - - -    SEQ ID NO 1
187 - - - - - - - W - - - - - - - - - - - - - - - T K R Y A - - - - - -    GI 1064914
142 - - - - - - - W - - - - - - - - - - - - - - - T K K Y A - - - - - -    GI 4718
195 S N K D M A D N F W Y D S D L D D D E N G S V I L Q D D D Y D D G N N H I P F E    GI 798905

201 - - - - - - - - - - - - - - - - - - - - - - - - - - - - - - - - -    SEQ ID NO 1
193 - - - - - - - - - - - - - - - - - - - - - - - - - - - - - - - - -    GI 1064914
148 - - - - - - - - - - - - - - - - - - - - - - - - - - - - - - - - -    GI 4718
235 D D D V Y N Y N D N D D D D E R I E F E D D D D D S I D N D S V M D R K Q    GI 798905

201 - - - - - - - - - - T - - - - - - - - - - - - - - - - - - - - - -    SEQ ID NO 1
193 - - - - - - - - - - T - - - - - - - - - - - - - - - - - - - - - -    GI 1064914
148 - - - - - - - - - - V - - - - - - - - - - - - - - - - - - - - - -    GI 4718
275 P H K A E D E S E D V E D V E R V S K K I                            GI 798905
```

FIGURE 3B

HUMAN UBIQUITIN-CONJUGATING ENZYME

FIELD OF THE INVENTION

The present invention relates to nucleic acid and amino acid sequences of a novel human ubiquitin-conjugating enzyme and to the use of these sequences in the diagnosis, study, prevention and treatment of disease.

BACKGROUND OF THE INVENTION

The ubiquitin system is a major pathway for selective protein degradation (Finley D et al (1991) Annu Rev Cell Biol 7:25–69). Degradation by this system is instrumental in a variety of cellular functions such as DNA repair, cell cycle progression, signal transduction, transcription, and antigen presentation. The ubiquitin pathway also eliminates proteins that are misfolded, misplaced, or that are in other ways abnormal. This pathway requires the covalent attachment of ubiquitin (E1), a highly conserved 76 amino acid protein, to defined lysine residues of substrate proteins.

Substrate recognition by this pathway involves a specialized recognition and targeting apparatus, the ubiquitin-conjugating system. Ubiquitin-conjugating enzyme (E2) and ubiquitin-protein ligase (E3), either independently or in conjunction, catalyze isopeptide formation between the carboxyl terminus of ubiquitin and amino groups of internal lysine residues of target proteins (Scheffner M et al (1995) Nature 373:81–83). Ubiquitin-protein conjugates are then recognized and degraded by a specific protease complex, the 26S proteasome. Both E2 and E3 exist as protein families, and their pattern of expression is thought to determine substrate specificity (Nuber U et al (1996) J Biol Chem 271:2795–2800).

The yeast ubiquitin-conjugating enzyme Ubc3 (also known as CDC34) plays a crucial role in the progression of the cell cycle from the G1 to S phase and the correct positioning of ubiquitin on a surface of Ubc3 is a requirement for this cell cycle transition (Prendergast J A et al (1995) J Biol Chem 270:9347–9352). Mutation studies have suggested that amino acids S-73, S-97, and S-139 of Ubc3 may be critical for substrate specificity, while C-95 is the site of catalytic activity (Liu Y et al (1995) Mol Cel Biol 15:5635–5644). An alteration in C-95 and another highly conserved amino acid, L-99, resulted in a dominant negative mutation (Banerjee A et al (1995) J Biol Chem 270:26209–26215). Overexpression of this mutation of Ubc3 was found to block cell growth in otherwise wild type strains.

Diseases and E2

A decrease in muscle mass, known as muscle wasting or cachexia, has been shown to be associated with the ubiquitin-dependent proteolytic system. Rats bearing the Yoshida AH-130 ascites hepatoma for 7 days showed a significant decrease in muscle mass in relation to non-tumor bearing controls (Llovera M et al (1995) Int J Cancer 61:138–141). The muscle wasting was found to be associated with an increased proteolytic rate related to the ubiquitin-dependent proteolytic system. Muscle wasting is common among human cancer patients. In addition to cancer, ubiquitin-dependent muscle wasting is also influenced by nutritional manipulation (such as fasting and dietary protein deficiency), muscle activity and disuse, AIDS, and the pathological conditions, sepsis, trauma, and acidosis (Attaix D et al (1994) Reprod Nutr Dev 34:583–597). In a rat model for long lasting sepsis, researchers found that E2 mRNA levels increase during the acute and chronic disease phases and parallel a rise in muscle protein breakdown (Voisin L et al (1996) J Clin Invest 97:1610–1617).

The presence of ubiquitin and ubiquitin conjugates has been detected in patients affected by neurodegenerative diseases such as Alzheimer's disease. Whereas the intracellular amyloid beta-protein precursor (APP) did not show appreciable ubiquitin-mediated degradation, three extracellular APP forms were degraded by this proteolytic pathway, suggesting a potential regulatory role for the ubiquitin-dependent system in the in vivo APP metabolic pathway (Gregori L et al (1994) Biochem Biophys Res Commun 203:1731–1738). Paired helical filaments (PHF) are fibrillar structures that accumulate in degenerating neurons in the brains of Alzheimer's disease patients. One component of PHF, the PHF-smear, consists of the tau protein fragment bound to ubiquitin (Morishima M et al (1994) Dementia 5:282–288).

Evidence from experiments on mouse and rabbit reticulocytes indicates that ubiquitin conjugation is a key rate-limiting step in antigen presentation (Grant E.P .et al (1995) J Immunol 155:3750–3758). The rates of degradation of beta-galactosidase constructs correlated with the rates of class I antigen presentation in vivo. This shows that ubiquitin degradation pathway may have a critical role in generating major histocompatibility complex (MHC) class I-presented peptides.

Depletion of specific cellular proteins may have many medical and agricultural benefits. Redirecting the ubiquitin-dependent proteolytic pathway may facilitate specific proteolytic removal. Gosink M. M. et al (1995, Proc Natl Acad Sci 92:9117–9121) report 5 examples in which E2 target recognition was redefined by engineering E2 to contain appropriate protein-binding peptides fused to their C termini. Thus, it may be possible to design E2 capable of directing the selective removal of many intracellular proteins, such as those implicated in the pathogenesis of Alzheimer's disease.

The selective modulation of E2 activity may allow successful management of the diseases associated with protein degradation, such as Alzheimer's disease, muscle wasting syndrome, and diseases in which undesired proteins may be targeted for degradation, such as viral infections and cancer. A newly discovered E2 may have novel specificity and could thus target a unique set of proteins for degradation.

SUMMARY OF THE INVENTION

The present invention discloses a novel human ubiquitin conjugating enzyme (UBCP), characterized as having homology among the ubicuitin-conjugating enzymes UbcH6, UBC3, and UBC4. Accordingly, the invention features a substantially purified ubicuitin-conjugating enzyme, as shown in amino acid sequence of SEQ ID NO:1, and having characteristics of the ubiquitin-conjugating enzyme family.

One aspect of the invention features isolated and substantially purified polynucleotides which encode UBCP. In a particular aspect, the polynucleotide is the nucleotide sequence of SEQ ID NO:2. In addition, the invention features polynucleotide sequences that hybridize under stringent conditions to SEQ ID NO:2.

A nucleic acid sequence encoding UBCP, oligonucleotides, peptide nucleic acids (PNA), fragments, portions or antisense molecules thereof, may be used in diagnostic assays of body fluids or biopsied tissues to detect the expression level of a nucleic acid encoding UBCP. For example, nucleic acid sequences encoding UBCP designed from SEQ ID NO:2 can be used to detect the presence of the mRNA transcripts in a patient or to monitor modulation of the transcripts during treatment.

The present invention relates, in part, to the inclusion of the polynucleotide encoding UBCP in an expression vector which can be used to transform host cells or organisms. Such transgenic hosts are useful for the production of UBCP. Substantially purified UBCP or fragments thereof may be useful as a pharmaceutical composition. For example, they may be used to inhibit or reverse the development of Alzheimer's disease or cancer.

Nucleic acid sequence encoding UBCP also provides for the design of antisense molecules useful in diminishing or eliminating expression of the genomic nucleotide sequence in conditions with which UBCP activity may be associated, such as cachexia.

The invention further provides diagnostic assays and kits for the detection of naturally occurring UBCP. It provides for the use of substantially purified UBCP as a positive control and to produce anti-UBcP antibodies which can be used to quantitate the amount of UBCP in human body fluids or biopsied tissues. UBCP can also be used to identify agonists, antagonists, or inhibitors which modulate the lifespan of the UBCP molecule in vivo.

The invention also relates to pharmaceutical compositions comprising UBCP, antisense molecules capable of disrupting expression of the genomic sequence encoding UBCP, and agonists, antibodies, antagonists or inhibitors of UBCP. These compositions are useful for the prevention or treatment of conditions associated with the expression of UBCP.

BRIEF DESCRIPTION OF THE FIGURES

FIGS. 1A and 1B show the amino acid sequence (SEQ ID NO:1) and nucleic acid sequence (SEQ ID NO:2) of the novel E2, UBCP produced using MACDNASIS software (Hitachi Software Engineering Co Ltd).

FIGS. 2A and 2B show the northern analysis for Incyte Clone 618887 (SEQ ID NO:2) produced electronically using LIFESEQ® database (Incyte Pharmaceuticals, Palo Alto Calif.). The percentage abundance is calculated by multiplying the number of transcripts found in the library times 100 and dividing the product by the total number of transcripts in the library.

FIGS. 3A and 3B show the amino acid sequence alignments among UBCP (SEQ ID NO:1), UbcH6 (GI 1064914; SEQ ID NO:3), yeast UBC4 (GI 4718; SEQ ID NO:4), and yeast UBC3 (GI 798905; SEQ ID NO:5) produced using the multisequence alignment program of DNASTAR software (DNAStar Inc, Madison Wis.).

DETAILED DESCRIPTION OF THE INVENTION

Definitions

Figure 4:
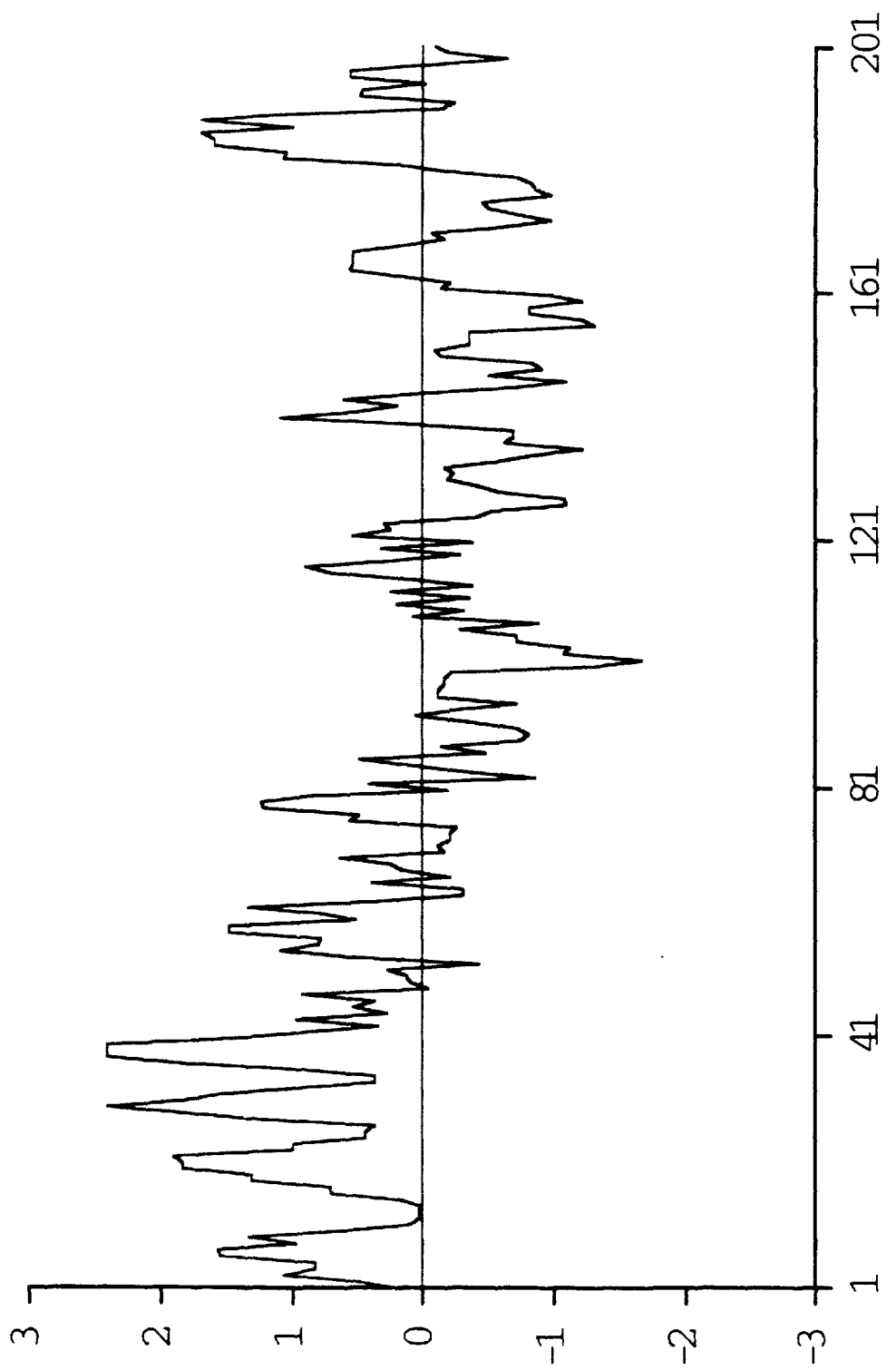
FIG. 4 shows the hydrophobicity plot (generated using MacDNAsis software) for UBCP, SEQ ID NO:1; the X axis reflects amino acid position, and the negative Y axis, hydrophobicity (FIGS. 4 and 5).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P. E. et al (1993) Anticancer Drug Des 8:53–63).

As used herein, UBCP refers to the amino acid sequence of substantially purified UBCP obtained from any species, particularly mammalian, including bovine, ovine, porcine, murine, equine, and preferably human, from any source whether natural, synthetic, semi-synthetic, or recombinant.

The present invention also encompasses UBCP variants. A preferred UBCP variant is one having at least 80% amino acid sequence similarity to the UBCP amino acid sequence (SEQ ID NO:1), a more preferred UBCP variant is one having at least 90% amino acid sequence similarity to SEQ ID NO:1, and a most preferred UBCP variant is one having at least 95% amino acid sequences similarity to SEQ ID NO:1.

A "variant" of UBCP may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a UBCP having structural, regulatory or biochemical functions of the naturally occurring UBCP. Likewise, "immunologically active" defines the capability of the natural, recombinant or synthetic UBCP, or any oligopeptide thereof, to induce a specific immune response in appropriate animals or cells and to bind with specific antibodies.

The term "derivative" as used herein refers to the chemical modification of a nucleic acid encoding UBCP or the encoded UBCP. Illustrative of such modifications would be replacement of hydrogen by an alkyl, acyl, or amino group. A nucleic acid derivative would encode a polypeptide which retains essential biological characteristics of natural UBCP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

Description

The present invention relates to the novel E2, UBCP, initially identified among the partial cDNAs from a paraganglionic tissue library (PGANNOT01) and to the use of the nucleic acid and amino acid sequences disclosed herein in the study, diagnosis, prevention and treatment of disease. cDNAs encoding a portion of UBCP were found in libraries from a large number of cell lines and normal or diseased tissues including many derived from tumors (FIGS. 2A and 2B).

Figure 5:
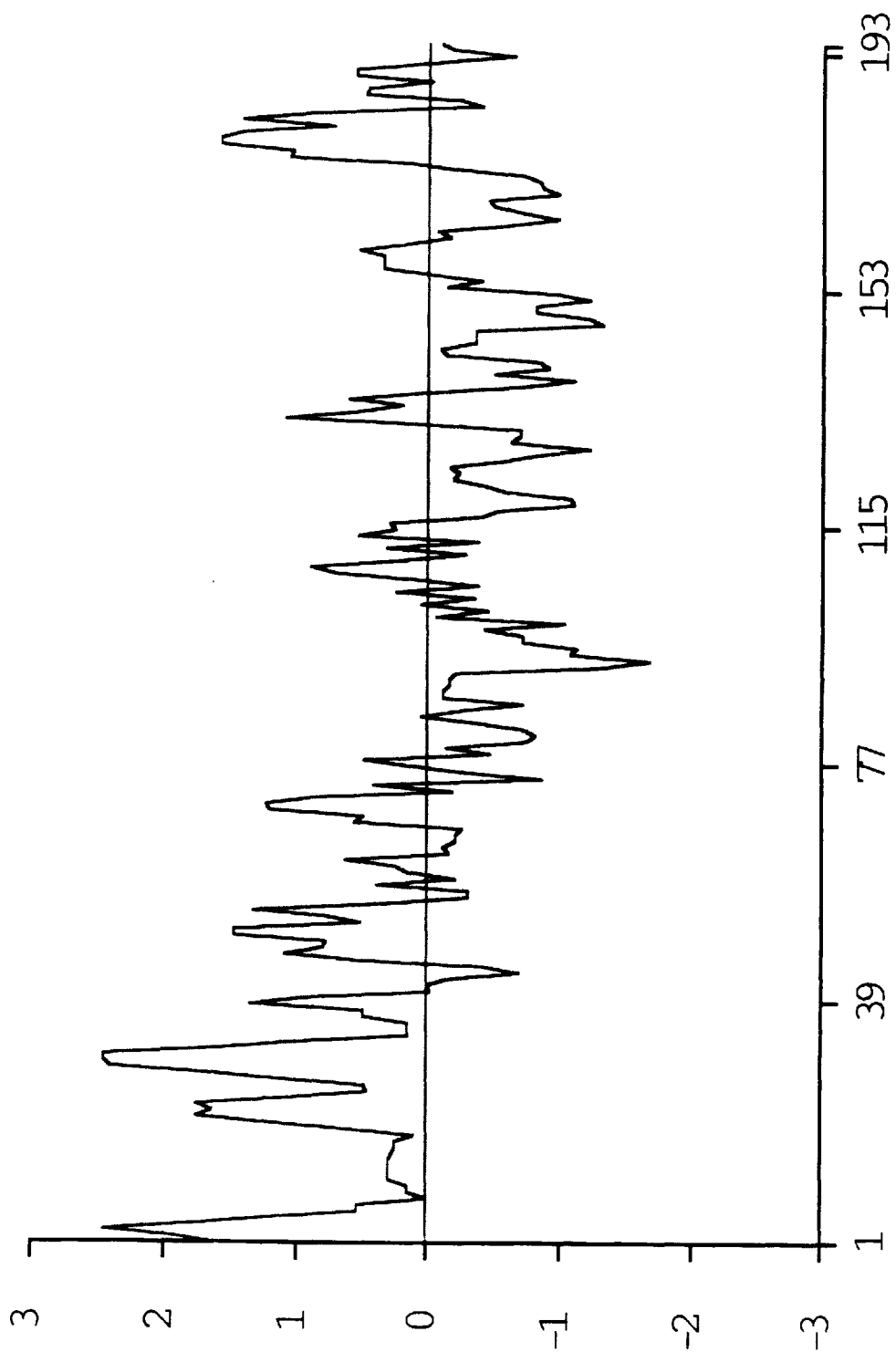
FIG. 5 shows the hydrophobicity plot for UbcH6.

Nucleic acid encoding a portion of UBCP was first identified in the cDNA, Incyte Clone 618887 (SEQ ID NO:2), through a computer-generated search for amino acid sequence alignments. The nucleic acid sequence, SEQ ID NO:2; disclosed herein and designated in lower case (ubcp)

encodes the amino acid sequence, SEQ ID NO:1, disclosed hereinafter as UBCP. The present invention is based, in part, on the chemical and structural homology among UBCP, UBCP, UbcH6 (GI 1064914; Nuber U et al (1996), J Biol Chem 271:2795–2800), yeast UBC4 (GI 4718; Seufert W et al (1990) EMBO J 9:543–550), and yeast UBC3 (CDC34) (GI 798905; Hunt S et al, unpublished; FIGS. 3A and 3B). UBCP has 84% identity in amino acid sequence to UbcH6. As illustrated by FIGS. 4 and 5, UBCP and GI 1064914 have similar hydrophobicity plots suggesting shared configuration and activity. UBCP is 201 amino acids long and has two potential glycosylation sites.

The UBCP Coding Sequences

The nucleic acid and deduced amino acid sequences of UBCP are shown in FIGS. 1A and 1B. In accordance with the invention, any nucleic acid sequence which encodes the amino acid sequence of UBCP can be used to generate recombinant molecules which express UBCP. In a specific embodiment described herein, a partial sequence of ubcp was first isolated as Incyte Clone 618887 from a paraganglionic tissue cDNA library (PGANNOT01).

It will be appreciated by those skilled in the art that as a result of the degeneracy of the genetic code, a multitude of UBCP-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring UBCP, and all such variations are to be considered as being specifically disclosed.

Although nucleotide sequences which encode UBCP and its variants are preferably capable of hybridizing to the nucleotide sequence of the naturally occurring UBCP under appropriately selected conditions of stringency, it may be advantageous to produce nucleotide sequences encoding UBCP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding UBCP and its derivatives without altering the encoded amino acid. sequences include the production of RNA transcripts having more desirable properties, such as a greater half-life, than transcripts produced from the naturally occurring sequence.

It is now possible to produce a DNA sequence, or portions thereof, encoding a UBCP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a ubcp sequence or any portion thereof.

Also included within the scope of the present invention are polynucleotide sequences that are capable of hybridizing to the nucleotide sequence of FIGS. 1A and 1B under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and confer may be used at a defined "stringency" as explained below.

"Maximum stringency" typically occurs at about Tm-5° C. (50° C. below the Tm of the probe); "high stringency" at about 5° C. to 100° C. below Tm; "intermediate stringency" at about 10° C. to 20° C. below Tm; and "low stringency" at about 200° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stocton Press, New York N.Y.). Amplification as carried out in the polymerase chain reaction technologies is described in Dieffenbach C. W. and G. S. Dveksler (1995, *PCR Primer, a Laboratory Manual*, Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring UBCP.

A "substitution" results from the replacement of one or more nucleotides or amino acids by different nucleotides or amino acids, respectively.

Altered ubcp nucleic acid sequences which may be used in accordance with the invention include deletions, insertions or substitutions of different nucleotides resulting in a polynucleotide that encodes the same or a functionally equivalent UBCP. The protein may also show deletions, insertions or substitutions of amino acid residues which produce a silent change and result in a functionally equivalent UBCP. Deliberate amino acid substitutions may be made on the basis of similarity in polarity, charge, solubility, hydrophobicity, hydrophilicity, and/or the amphipathic nature of the residues as long as the biological activity of UBCP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalamine and tyrosine.

Included within the scope of the present invention are alleles of UBCP. As used herein, an "allele" or "allelic sequence" is an alternative form of UBCP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions, or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE DNA polymerase (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton MICRO LAB 2200 (Hamilton, Reno Nev.), Peltier thermal cycler (PTC200; MJ Research, Watertown Mass.) and the ABI 377 DNA sequencers (Perkin Elmer).

Extending the Polynucleotide Sequence

The polynucleotide sequence of ubcp may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO 406 primer analysis software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method for targeted gene walking which permits retrieval of unknown sequence. PROMO-TERMINDER a new kit available from Clontech (Palo Alto CA) uses PCR, nested primers and PromoterFinder libraries to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. GENOTYPER AND SEQUENCE NAVIGATOR software from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851–8).

Expression of the Nucleotide Sequence

In accordance with the present invention, polynucleotide sequences which encode UBCP, fragments of the polypeptide, fusion proteins or functional equivalents thereof may be used in recombinant DNA molecules that direct the expression of UBCP in appropriate host cells. Due to the inherent degeneracy of the genetic code, other DNA sequences which encode substantially the same or a functionally equivalent amino acid sequence, may be used to clone and express UBCP. As will be understood by those of skill in the art, it may be advantageous to produce UBCP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of UBCP expression or to produce recombinant RNA transcripts having desirable properties, such as a longer half-life, than transcripts produced from naturally occurring sequence.

The nucleotide sequences of the present invention can be engineered in order to alter a UBCP coding sequence for a variety of reasons, including but not limited to, alterations which modify the cloning, processing, and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified, or recombinant ubcp sequence may be ligated to a heterologous sequence to encode a fusion protein. For example, for screening of peptide libraries for inhibitors of UBCP activity, it may be useful to encode a chimeric UBCP protein that is recognized by a commercially available antibody. A fusion protein may also be engineered to contain a cleavage site located between a UBCP sequence and the heterologous protein sequence, so that the UBCP may be cleaved and purified away from the heterologous moiety.

In an alternate embodiment of the invention, the coding sequence of UBCP could be synthesized, whole or in part, using chemical methods well known in the art (see Caruthers M. H. et al (1980) Nuc Acids Res Symp Ser 215–23, Horn T et al(1980) Nuc Acids Res Symp Ser 225–32, etc). Alternatively, the protein itself could be produced using chemical methods to synthesize a UBCP amino acid sequence, whole or in part. For example, peptide synthesis can be performed using various solid-phase techniques (Roberge J. Y. et al (1995) Science 269:202–204) and automated synthesis may be achieved, for example, using the ABI 431A peptide synthesizer (Perkin Elmer) in accordance with the instructions provided by the manufacturer.

The newly synthesized peptide can be substantially by preparative high performance liquid chromatography (eg, Creighton (1983) *Proteins, Structures and Molecular Principles,* W H Freeman and Co, New York N.Y.). The composition of the synthetic peptides may be confirmed by amino acid analysis or sequencing (eg, the Edman degradation procedure; Creighton, supra). Additionally the amino acid sequence of UBCP, or any part thereof, may be altered during direct synthesis and/or combined using chemical methods with sequences from other proteins, or any part thereof, to produce a variant polypeptide.

Expression Systems

In order to express a biologically active UBCP, the nucleotide sequence encoding UBCP or its functional equivalent, is inserted into an appropriate expression vector, ie, a vector which contains the necessary elements for the transcription and translation of the inserted coding sequence.

Methods which are well known to those skilled in the art can be used to construct expression vectors containing a UBCP coding sequence and appropriate transcriptional or translational controls. These methods include in vitro recombinant DNA techniques, synthetic techniques, and in vivo recombination or genetic recombination. Such techniques are described in Sambrook et al (1989) *Molecular Cloning, A Laboratory Manual,* Cold Spring Harbor Press, Plainview N.Y. and Ausubel F. M. et al (1989) *Current Protocols in Molecular Biology,* John Wiley & Sons, New York N.Y.

A variety of expression vector/host systems may be utilized to contain and express a UBCP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities, and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of UBCP, vectors based on SV40 or EBV may be used with an appropriate selectable marker.

In bacterial systems, a number of expression vectors may be selected depending upon the use intended for UBCP. For example, when large quantities of UBCP are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the UBCP coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. PGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al (supra) and Grant et al (1987) Methods in Enzymology 153:516–544.

In cases where plant expression vectors are used, the expression of a sequence encoding UBCP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R.M. (1991) Results Probl Cell Differ 17:85–105) may be used. These constructs can be introduced into plant cells by direct DNA transformation or pathogen-mediated transfection. For reviews of such techniques, see Hobbs S or Murry L. E. in McGraw Hill *Yearbook of Science and Technology* (1992) McGraw Hill New York N.Y., pp 191–196 or Weissbach and Weissbach (1988) *Method for Plant Molecular Biology,* Academic Press, New York N.Y., pp 421–463.

An alternative expression system which could be used to express UBCP is an insect system. In one such system, *Autographa californica* nuclear polyhedrosis virus (AcNPV) is used as a vector to express foreign genes in *Spodoptera frugiperda* cells or in Trichoplusia larvae. The UBCP coding sequence may be cloned into a nonessential region of the virus, such as the polyhedrin gene, and placed under control of the polyhedrin promoter. Successful insertion of UBCP will render the polyhedrin gene inactive and produce recombinant virus lacking coat protein coat. The recombinant viruses are then used to infect *S. frugiperda* cells or Trichoplusia larvae in which UBCP is expressed (Smith et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, a UBCP coding sequence may be ligated into an adenovirus transcription/translation complex consisting of the late promoter and tripartite leader sequence. Insertion in a nonessential E1 or E3 region, of the viral genome will result in a viable virus capable of expressing UBCP in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a UBCP sequence. These signals include the ATG initiation codon and adjacent sequences. In cases where UBCP, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express UBCP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C. A. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the UBCP is inserted within a marker gene sequence, recombinant cells containing UBCP can be identified by the absence of marker gene function. Alternatively, a marker gene can be placed in tandem with a UBCP sequence under the control of a single promoter. Expression of the marker gene in response to induction or selection usually indicates expression of the tandem UBCP as well.

Alternatively, host cells which contain the coding sequence for UBCP and express UBCP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the ubcp polynucleotide sequence can be detected by DNA-DNA or DNA-RNA hybridization or amplification using probes, portions, or fragments of ubcp. Nucleic acid amplification based assays involve the use of oligonucleotides or oligomers based on the ubcp sequence to detect transformants containing ubcp DNA or RNA. As used herein "oligonucleotides" or "oligomers" refer to a nucleic acid sequence of preferably at least about 10–60 nucleotides, more preferably 15–30 nucleotides, and most preferably 20–25 nucleotides, which can be used as a probe or amplimer.

A variety of protocols for detecting and measuring the expression of UBCP, using either polyclonal or monoclonal antibodies specific for the protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on UBCP is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to ubcp include oligolabeling, nick translation, end-labeling or PCR amplification using a labeled nucleotide. Alternatively, the UBCP sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include, U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567, incorporated herein by reference.

Purification of UBCP

Host cells transformed with a ubcp nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing ubcp can be designed with signal sequences which direct secretion of UBCP through a prokaryotic or eukaryotic cell membrane. Other recombinant constructions may join UBCP to nucleotide sequence encoding a polypeptide domain which will facilitate purification of soluble proteins (Kroll D. J. et al (1993) DNA Cell Biol 12:441–53; cf discussion of vectors infra containing fusion proteins).

UBCP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp, Seattle Wash.). The inclusion of a cleavable linker sequences such as Factor XA or enterokinase (Invitrogen, San Diego Calif.) between the purification domain and UBCP is useful to facilitate purification. One such expression vector provides for expression of a fusion protein compromising an UBCP and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3:263–281) while the enterokinase cleavage site provides a means for purifying the chemokine from the fusion protein.

In addition to recombinant production, fragments of UBCP may be produced by direct peptide synthesis using solid-phase techniques (cf Stewart et al (1969) *Solid-Phase Peptide Synthesis,* W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of UBCP may be chemically synthesized separately and combined using chemical methods to produce the full length molecule.

Uses of UBCP

The rationale for use of the nucleotide and polypeptide sequences disclosed herein is based in part on the chemical and structural homology among the novel human UBCP disclosed herein, human UbcH6 (GI 1064914; Nuber et al, supra), yeast UBC4 (GI 4718; Seufert et al, supra), and yeast UBC3 (GI 798905; Hunt et al, supra; FIGS. 3A and 3B).

Banerjee et al (1995; supra) found that overexpression of a mutation of Ubc3 blocked cell growth in otherwise wild type yeast strains. Similarly, UBCP or a UBCP derivative, delivered in suitable form, may block tumor cell growth.

Gregori et al (1994; supra) found evidence for a regulatory role for the ubiquitin-dependent proteolytic system in the in vivo APP metabolic pathway and Morishima et al (1994; supra) found ubiquitin associated with PHF in degenerating neurons in the brains of Alzheimer's disease patients. Therefore, UBCP or a UBCP derivative, delivered in suitable form, may alter the production of APP and/or PHF and benefit Alzheimer's disease patients.

Grant et al (1995; supra) found that ubiquitin conjugation is a key rate-limiting step in antigen presentation. Since the ubiquitin degradation pathway may have a critical role in generating major histocompatibility complex (MHC) class I-presented peptides, changes in the activity of E2s, such as UBCP, may alter antigen presentation. In the case of autoimmune diseases, such as multiple sclerosis or asthma, it would be advantageous to reduce specific antigen presentation, whereas in treating cancer it may advantageous to increase specific tumor associated antigen presentation. Thus, UBCP activity may be modulated to alter immune system function so as to treat cancer and autoimmune diseases.

Muscle wasting has been found to be associated with the ubiquitin pathway of protein degradation in cancer, AIDS, and sepsis (Attaix et al supra; Llovera et al 1995 supra; Voisin et al 1996, supra). An inhibitor of UBCP may slow or stop the progression of muscle wasting in patients with cancer, AIDS, sepsis, or other conditions.

Gosink et al (1995; supra) suggested that E2s may be engineered so that specific proteins are targeted for degradation. UBCP may be suitable for such engineering. UBCP may be altered in such a way as to target and therefore degrade potentially harmful proteins, such as APP in Alzheimer's disease patients. UBCP may also be engineered to target and degrade foreign proteins, such as those made by a harmful virus.

In disorders or conditions where it is desirable to limit UBCP associated protein degradation, cells could be transfected with antisense sequences of ubcp or provided with inhibitors of UBCP so as to lessen the breakdown of such proteins.

UBCP Antibodies

UBCP-specific antibodies are useful for the diagnosis of conditions and diseases associated with expression of UBCP. UBCP for antibody induction does not require biological activity; however, the protein fragment, or oligopeptide must be antigenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small, naturally occurring molecule. Short stretches of UBCP amino acids may be fused with those of another protein such as keyhole limpet hemocyanin and antibody produced against the chimeric molecule. Procedures well known in the art can be used for the production of antibodies to UBCP Such antibodies include, but are not limited to, polyclonal, monoclonal, chimeric, single chain, Fab fragments, and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc may be immunized by injection with UBCP or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to UBCP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy,* Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce UBCP-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86:3833–3837), and Winter G and Milstein C (1991; Nature 349:293–299).

Antibody fragments which contain specific binding sites for UBCP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W. D. et al (1989) Science 256:1275–1281).

A variety of protocols for competitive binding or immunoradiometric assays using either polyclonal or monoclonal antibodies with established specificities are well known in the art. Such immunoassays typically involve the formation of complexes between UBCP and its specific antibody and the measurement of complex formation. A two-site, monoclonal-based immunoassay utilizing monoclonal antibodies reactive to two noninterfering epitopes on a specific UBCP protein is preferred, but a competitive binding assay may also be employed. These assays are described in Maddox D.E. et al (1983, J Exp Med 158:1211).

Diagnostic Assays Using UBCP Specific Antibodies

Particular UBCP antibodies are useful for the diagnosis of conditions or diseases characterized by expression of UBCP or in assays to monitor patients being treated with UBCP, agonists, or inhibitors. Diagnostic assays for UBCP include methods utilizing the antibody and a label to detect UBCP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring UBCP, using either polyclonal or monoclonal antibodies specific for the respective protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on UBCP is preferred, but a competitive binding assay may be employed. These assays are described, among other places, in Maddox, D.E. et al (1983, J Exp Med 158:1211).

In order to provide a basis for diagnosis, normal or standard values for UBCP expression must be established. This is accomplished by combining body fluids or cell extracts taken from normal subjects, either animal or human, with antibody to UBCP under conditions suitable for complex formation which are well known in the art. The amount of standard complex formation may be quantified by comparing various artificial membranes containing known quantities of UBCP with both control and disease samples from biopsied tissues. Then, standard values obtained from normal samples may be compared with values obtained from samples from subjects potentially affected by disease. Deviation between standard and subject values establishes the presence of disease state.

Drug Screening

UBCP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between UBCP and the agent being tested, may be measured.

Another technique for drug screening which provides for high throughput screening of compounds having suitable binding affinity to the UBCP is described in detail in "Determination of Amino Acid Sequence Antigenicity" by Geysen H. N., WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of UBCP and washed. Bound UBCP is then detected by methods well known in the art. Purified UBCP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding UBCP specifically compete with a test compound for binding UBCP. In this manner, the antibodies can be used to detect the presence of any peptide which shares one or more antigenic determinants with UBCP.

Uses of the Polynucleotide Encoding UBCP

A polynucleotide, ubcp, or any part thereof, may be used for diagnostic and/or therapeutic purposes. For diagnostic purposes, the ubcp of this invention may be used to detect and quantitate gene expression in biopsied tissues in which expression of UBCP may be implicated. The diagnostic assay is useful to distinguish between absence, presence, and excess expression of UBCP and to monitor regulation of UBCP levels during therapeutic intervention. Included in the scope of the invention are oligonucleotide sequences, anti-sense RNA and DNA molecules, and PNAs.

Another aspect of the subject invention is to provide for hybridization or PCR probes which are capable of detecting polynucleotide sequences, including genomic sequences, encoding UBCP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or, low) will determine whether the probe identifies only naturally occurring ubcp, alleles or related sequences.

Probes may also be used for the detection of related sequences and should preferably contain at least 50% of the nucleotides from any of these UBCP encoding sequences. The hybridization probes of the subject invention may be derived from the nucleotide sequence of SEQ ID NO:2 or from genomic sequence including promoter, enhancer elements and introns of the naturally occurring UBCP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for ubcp DNAs include the cloning of nucleic acid sequences encoding UBCP or UBCP derivatives into vectors for the production of mRNA probes. Such vectors are known in the art and are commercially available and may be used to synthesize RNA probes in vitro by means of the addition of the appropriate RNA polymerase such as T7 or SP6 RNA polymerase and the appropriate radioactively labeled nucleotides.

Diagnostics

Polynucleotide sequences encoding UBCP may be used for the diagnosis of conditions or diseases with which the expression of UBCP is associated. For example, polynucleotide sequences encoding UBCP may be used in hybridization or PCR assays of fluids or tissues from biopsies to detect UBCP expression. The form of such qualitative or quantitative methods may include Southern or northern analysis, dot blot or other membrane-based technologies; PCR technologies; dip stick, pin, chip, and ELISA technologies. All of these techniques are well known in the art and are the basis of many commercially available diagnostic kits.

The ubcp nucleotide sequences disclosed herein provide the basis for assays that detect activation or induction associated with muscle wasting. The ubcp nucleotide sequence may be labeled by methods known in the art and added to a fluid or tissue sample from a patient under conditions suitable for the formation of hybridization complexes. After an incubation period the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of ubcp nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for UBCP expression must be established. This is accomplished by combining body fluids or cell extracts taken from normal subjects, either animal or human, with UBCP, or a portion thereof, under conditions suitable for hybridization or amplification. Standard hybridization may be quantified by comparing the values obtained for normal subjects with a dilution series of UBCP run in the same experiment where a known amount of a substantially purified UBCP is used. Standard values obtained from normal samples may be compared with values obtained from samples from patients affected by UBCP-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the UBCP sequence. Such oligomers are generally chemically synthesized, but they may be generated enzymatically or produced from a recombinant source. Oligomers generally comprise two nucleotide sequences, one with sense orientation (5'->3') and one with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby P. C. et al 1993 J Immunol Methods 159:235–44) or biotinylating (Duplaa C et al 1993 Anal Biochem 212:229–36 nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of a relatively high amount of UBCP in extracts of biopsied tissues may indicate the onset of muscle wasting. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutics

Based upon its homology to genes encoding ubiquitin-conjugating enzymes and its expression profile, the ubcp polynucleotide disclosed herein may be useful in the treatment of disorders such as Alzheimer's disease, cancer, muscle wasting due to AIDS, cancer, sepsis, or other causes, and viral infections, including HIV infection.

Expression vectors derived from retroviruses, adenovirus, herpes, or vaccinia viruses, or from various bacterial plasmids, may be used for delivery of nucleotide sequences to the targeted organ, tissue or cell population. Methods which are well known to those skilled in the art can be used to construct recombinant vectors which will express antisense ubcp. See, for example, the techniques described in Sambrook et al (supra) and Ausubel et al (supra).

The polynucleotides comprising full length cDNA sequence and/or its regulatory elements enable researchers to use ubcp as an investigative tool in sense (Youssoufian H and H. F. Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding UBCP can be turned off by transfecting a cell or tissue with expression vectors which express high levels of a desired ubcp fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA or PNA, to the control regions of ubcp, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al (In: Huber B. E. and B. I. Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of ubcp.

Specific ribozyme cleavage sites within any potential RNA target are initially identified by scanning the target molecule for ribozyme cleavage sites which include the following sequences, GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding UBCP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, incorporated herein by reference. Delivery by transfection and by liposome are quite well known in the art.

Furthermore, the nucleotide sequences for UBCP disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for UBCP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

The technique of fluorescent in situ hybridization of chromosome spreads has been described, among other places, in Verma et al (1988) *Human Chromosomes: A Manual of Basic Techniques,* Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of ubcp on a physical chromosomal map and a specific disease (or predisposition to a specific disease) may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T. J. et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs, or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of UBCP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that UBCP or an UBCP derivative can be delivered in a suitable formulation to direct the degradation of specific proteins. Such treatment could prevent the onset of Alzheimer's disease. Similarly, administration of UBCP antagonists may also inhibit the activity or shorten the lifespan of this protein and lessen the onset and progression of muscle wasting in AIDS, cancers, and other diseases.

The examples below are provided to illustrate the subject invention and are not included for the purpose of limiting the invention.

EXAMPLES

I DNA Library Construction

The normal tissue used for paraganglion cDNA library construction was obtained from a 46 year-old male The frozen tissue was homogenized and lysed in guanidinium isothiocyanate solution using a Brinkmann Homogenizer Polytron PT-3000 (Brinkmann Instruments, Westbury N.J.). The lysate was centrifuged over a 5.7M CsCl cushion using an Beckman SW28 rotor in a Beckman L8–70M Ultracentrifuge (Beckman Instruments) for 18 hours at 25,000 rpm at ambient temperature. The RNA was extracted twice with acid phenol pH 4.0 following Stratagene's RNA isolation protocol and precipitated using 0.3M sodium acetate and 2.5 volumes of ethanol, resuspended in DEPC-treated water and DNase treated for 15 min at 37° C. The reaction was stopped with an equal volume of acid phenol, and the RNA was isolated using the Qiagen OLIGOTEX kit (QIAGEN Inc, Chatsworth Calif.) and used to construct the cDNA library.

The RNA was handled according to the recommended protocols in the SUPERSCRIPT plasmid system for cDNA synthesis and plasmid cloning (catalog #18248-013; Gibco/BRL), and cDNAs were ligated in PSPORT1 plasmid. The plasmid PSPORT1 was subsequently transformed into DH5α competent cells (Cat. #18258-012, Gibco/BRL).

II Isolation and Sequencing of CDNA Clones

Plasmid DNA was released from the cells and substantially purified using the MINIPREP Kit (Catalogue #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @82900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS DNA purification System (Catalogue #A7100, Promega, Madison Wis.) or QIA WELL-8 plasmid, QIA WELL PLUS DNA, and QIA WELL ULTRA DNA purification Systems (QIAGEN® Chatsworth Calif.).

The cDNAs were sequenced by the method of Sanger F and A. R. Coulson (1975; J Mol Biol 94:441f), using a Hamilton MICROLAB 2200 (Hamilton, Reno Nev.) in combination with four Peltier thermal cyclers (PTC200 from MJ Research, Watertown Mass.) and Applied Biosystems 377 or 373 DNA sequencing systems (Perkin Elmer), and the reading frame was determined.

III Homology Searching of CDNA Clones and Their Deduced Proteins

Each CDNA was compared to sequences in GenBank using a search algorithm developed by Applied Biosystems and incorporated into the INHERIT 670 Sequence analysis system. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul S. F. 1993 and 1990, supra) are used to search for identical or related molecules in nucleotide databases such as GenBank or the LIFESEQ® database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of ubcp to Full Length or to Recover Regulatory Elements

The nucleic acid sequence of full length ubcp (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known ubcp sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO 4.06 primer analysis software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK DNA gel purification Kit (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 40° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 Software (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with SEPHADEX G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes NYTRAN PLUS membrane, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ (Kodak, Rochester N.Y.) is exposed to the blots, or alternatively, the blots are placed in a PHOSPHOIMAGER cassette (Molecular Dynamics, Sunnyvale Calif.) for several hours, hybridization patterns are compared visually.

VII Antisense Molecules

The ubcp sequence, or any part thereof, is used to inhibit in vivo or in vitro expression of naturally occurring UBCP. Although use of antisense oligonucleotides, comprising about 20 base-pairs, is specifically described, essentially the same procedure is used with larger cDNA fragments. An oligonucleotide based on the coding sequence of ubcp as shown in FIGS. 1A and 1B is used to inhibit expression of naturally occurring UBCP. The complementary oligonucleotide is designed from the most unique 5' sequence as shown in FIGS. 1A and 1B and used either to inhibit transcription by preventing promoter binding to the upstream nontranslated sequence or translation of an ubcp transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII Expression of UBCP

Expression of the UBCP is accomplished by subcloning the cDNAs into appropriate vectors and transfecting the vectors into host cells. In this case, the cloning vector, pSport, previously used for the generation of the cDNA library is used to express UBCP in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length ubcp. The signal sequence directs the secretion of UBCP into the bacterial growth media which can be used directly in the following assay for activity.

IX UBCP Activity

UBCP activity can be assessed by measuring the ability to form thioester adducts with ubiquitin in the presence of E1 (Jentsch S (1992) Ann Rev Genet 26:177–205). Nuber et al (supra) describe one such procedure. Reaction mixtures include approximately 5–10 ng of E1, 1 ug of $^{32}$P-labeled GST-ubiquitin, 100 ng of UBCP, a negative, or a positive E1 control in 30 mM TRIS-HCl, pH 7.6, 50 mM NaCl, 4 mM ATP, 10 mM $MgCl_2$, 0.2 mM dithiothreitol. After 5 min at 25° C., reactions are terminated by incubating the mixtures for 15 min at 30° C. in 50 mM TRIS-HCl, pH 6.8, 4M urea, 2% SDS, 10% glycerol. The whole reaction mixtures are separated on 10% SDS-polyacrylamide gels at 4° C. and radioactively labeled bands visualized by autoradiography.

X Production of UBCP Specific Antibodies

UBCP substantially purified using PAGE electrophoresis (Sambrook, supra) is used to immunize rabbits and to produce antibodies using standard protocols. The amino acid sequence translated from UBCP is analyzed using DNAStar software (DNASTAR Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 4 and 5) is described by Ausubel F.M. et al (supra).

Typically, the oligopeptides are 15 residues in length, synthesized using an Applied Biosystems peptide synthesizer model 431A using fmoc-chemistry, and coupled to keyhole limpet hemocyanin (KLH, Sigma) by reaction with M-maleimidobenzoyl-N-hydroxysuccinimide ester (MBS; Ausubel F.M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally occurring UBCP Using Specific Antibodies

Naturally occurring or recombinant UBCP is substantially purified by immunoaffinity chromatography using antibodies specific for UBCP. An immunoaffinity column is constructed by covalently coupling UBCP antibody to an activated chromatographic resin such as CnBr-activated SEPHAROSE (Pharmacia Biotech). After the coupling, the resin is blocked and washed according to the manufacturer's instructions.

Media containing UBCP is passed over the immunoaffinity column, and the column is washed under conditions that allow the preferential absorbance of UBCP (eg, high ionic strength buffers in the presence of detergent). The column is eluted under conditions that disrupt antibody/UBCP binding (eg, a buffer of pH 2–3 or a high concentration of a chaotrope such as urea or thiocyanate ion), and UBCP is collected.

XII Identification of Molecules Which Interact with UBCP

UBCP, or biologically active fragments thereof, are labelled with $^{125}$I Bolton-Hunter reagent (Bolton, A. E. and Hunter, W. M. (1973) Biochem J 133:529). Candidate molecules previously arrayed in the wells of a 96 well plate are incubated with the labelled UBCP, washed and any wells with labelled UBCP complex are assayed. Data obtained using different concentrations of UBCP are used to calculate values for the number, affinity, and association of UBCP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide encoding a polypeptide consisting of the amino acid sequence of SEQ ID NO:1.

2. An isolated and purified polynucleotide consisting of the sequence of SEQ ID NO:2, or a polynucleotide fully complementary to the sequence of SEQ ID NO:2.

3. An expression vector containing the polynucleotide of claim 1.

4. A host cell comprising the polynucleotide of claim 1.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 201 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: PGANNOT01
        ( B ) CLONE: 61887

( x i ) SEQUENCE DESCRIPTION: SEQ ID NO:1:

```
Met Ser Thr Glu Ala Gln Arg Val Asp Asp Ser Pro Ser Thr Ser Gly
 1               5                  10                 15
Gly Ser Ser Asp Gly Asp Gln Arg Glu Ser Val Gln Gln Glu Pro Glu
             20                 25                 30
Arg Glu Gln Val Gln Pro Lys Lys Lys Glu Gly Lys Ile Ser Ser Lys
         35                 40                 45
Thr Ala Ala Lys Leu Ser Thr Ser Ala Lys Arg Ile Gln Lys Glu Leu
     50                 55                 60
Ala Glu Ile Thr Leu Asp Pro Pro Pro Asn Cys Ser Ala Gly Pro Lys
 65                 70                 75                 80
Gly Asp Asn Ile Tyr Glu Trp Arg Ser Thr Ile Leu Gly Pro Pro Gly
                 85                 90                 95
Ser Val Tyr Glu Gly Gly Val Phe Phe Leu Asp Ile Thr Phe Ser Pro
            100                105                110
Asp Tyr Pro Phe Lys Pro Pro Lys Val Thr Phe Arg Thr Arg Ile Tyr
        115                120                125
His Cys Asn Ile Asn Ser Gln Gly Val Ile Cys Leu Asp Ile Leu Lys
    130                135                140
Asp Asn Trp Ser Pro Ala Leu Thr Ile Ser Lys Val Leu Leu Ser Ile
145                150                155                160
Cys Ser Leu Leu Thr Asp Xaa Asn Pro Ala Asp Pro Leu Val Gly Ser
                165                170                175
Ile Ala Thr Gln Tyr Met Thr Asn Arg Ala Glu His Asp Arg Xaa Ala
            180                185                190
Arg Gln Trp Thr Lys Arg Tyr Ala Thr
            195                200
```

( 2 ) INFORMATION FOR SEQ ID NO:2:

( i ) SEQUENCE CHARACTERISTICS:
        ( A ) LENGTH: 747 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: PGANNOT01
        ( B ) CLONE: 61887

( x i ) SEQUENCE DESCRIPTION: SEQ ID NO:2:

```
GCTCCCGGAG  GTGGTGGCTT  CACTTTCCAG  GACTCAGGGG  CAGCCACAGC  GACAGCCGCG      60

GGCAGCAGCC  TCAGGAGCCG  GAGCTGGAAC  GGCCGGGGGC  GGCGGCAGCG  GCGGCGCTGA     120

GGGATCTAAA  ATGTCCACTG  AGGCACAAAG  AGTTGATGAC  AGTCCAAGCA  CTAGTGGAGG     180

AAGTTCCGAT  GGAGATCAAC  GTGAAAGTGT  TCAGCAAGAA  CCAGAAAGAG  AACAAGTTCA     240

GCCCAAGAAA  AAGGAGGGAA  AAATATCCAG  CAAAACCGCT  GCTAAATTGT  CAACTAGTGC     300

TAAAAGAATT  CAGAAGGAAC  TTGCAGAAAT  CACATTGGAC  CCTCCTCCCA  ACTGTAGTGC     360

TGGACCCAAA  GGAGACAACA  TTTATGAATG  GAGGTCAACT  ATATTGGGAC  CCCCAGGATC     420

TGTCTATGAA  GGAGGGGTGT  TCTTTCTTGA  CATTACCTTT  TCACCAGACT  ATCCGTTTAA     480

ACCCCCTAAG  GTTACCTTCC  GAACAAGAAT  CTATCACTGT  AATATTAACA  GCCAAGGTGT     540

GATCTGTCTG  GACATCTTAA  AGGACAACTG  GAGTCCGGCT  TTAACTATTT  CTAAAGTTCT     600

CCTCTCCATC  TGCTCACTTC  TTACAGATTG  NAACCCTGCT  GACCCTCTGG  TGGGCAGCAT     660

CGCCACACAG  TACATGACCA  ACAGAGCAGA  GCATGACCGG  NTGGCCAGAC  AGTGGACCAA     720

GCGGTACGCC  ACATAGGGGC  CTGCTGT                                           747
```

( 2 ) INFORMATION FOR SEQ ID NO:3:

( i ) SEQUENCE CHARACTERISTICS:
        ( A ) LENGTH: 193 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 1064914

( x i ) SEQUENCE DESCRIPTION: SEQ ID NO:3:

```
Met  Ser  Asp  Asp  Asp  Ser  Arg  Ala  Ser  Thr  Ser  Ser  Ser  Ser  Ser
  1                  5                        10                       15

Ser  Ser  Asn  Gln  Gln  Thr  Glu  Lys  Glu  Thr  Asn  Thr  Pro  Lys  Lys
               20                        25                       30

Glu  Ser  Lys  Val  Ser  Met  Ser  Lys  Asn  Ser  Lys  Leu  Leu  Ser  Thr  Ser
          35                        40                       45

Ala  Lys  Arg  Ile  Gln  Lys  Glu  Leu  Ala  Asp  Ile  Thr  Leu  Asp  Pro  Pro
     50                        55                       60

Pro  Asn  Cys  Ser  Ala  Gly  Pro  Lys  Gly  Asp  Asn  Ile  Tyr  Glu  Trp  Arg
65                        70                        75                       80

Ser  Thr  Ile  Leu  Gly  Pro  Pro  Gly  Ser  Val  Tyr  Glu  Gly  Gly  Val  Phe
               85                        90                       95

Phe  Leu  Asp  Ile  Thr  Phe  Thr  Pro  Glu  Tyr  Pro  Phe  Lys  Pro  Pro  Lys
               100                      105                     110

Val  Thr  Phe  Arg  Thr  Arg  Ile  Tyr  His  Cys  Asn  Ile  Asn  Ser  Gln  Gly
          115                      120                       125

Val  Ile  Cys  Leu  Asp  Ile  Leu  Lys  Asp  Asn  Trp  Ser  Pro  Ala  Leu  Thr
     130                      135                       140

Ile  Ser  Lys  Val  Leu  Leu  Ser  Ile  Cys  Ser  Leu  Leu  Thr  Asp  Cys  Asn
145                           150                       155                    160

Pro  Ala  Asp  Pro  Leu  Val  Gly  Ser  Ile  Ala  Thr  Gln  Tyr  Met  Thr  Asn
               165                      170                       175

Arg  Ala  Glu  His  Asp  Arg  Met  Ala  Arg  Gln  Trp  Thr  Lys  Arg  Tyr  Ala
          180                      185                       190

Thr
```

( 2 ) INFORMATION FOR SEQ ID NO:4:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 4718

( x i ) SEQUENCE DESCRIPTION: SEQ ID NO:4:

```
Met Ser Ser Ser Lys Arg Ile Ala Lys Glu Leu Ser Asp Leu Glu Arg
 1               5                  10                  15

Asp Pro Pro Thr Ser Cys Ser Ala Gly Pro Val Gly Asp Asp Leu Tyr
            20                  25                  30

His Trp Gln Ala Ser Ile Met Gly Pro Ala Asp Ser Pro Tyr Ala Gly
         35                  40                  45

Gly Val Phe Phe Leu Ser Ile His Phe Pro Thr Asp Tyr Pro Phe Lys
     50                  55                  60

Pro Pro Lys Ile Ser Phe Thr Thr Lys Ile Tyr His Pro Asn Ile Asn
 65                  70                  75                  80

Ala Asn Gly Asn Ile Cys Leu Asp Ile Leu Lys Asp Gln Trp Ser Pro
                 85                  90                  95

Ala Leu Thr Leu Ser Lys Val Leu Leu Ser Ile Cys Ser Leu Leu Thr
                    100                 105                 110

Asp Ala Asn Pro Asp Asp Pro Leu Val Pro Glu Ile Ala His Ile Tyr
             115                 120                 125

Lys Thr Asp Arg Pro Lys Tyr Glu Ala Thr Ala Arg Glu Trp Thr Lys
     130                 135                 140

Lys Tyr Ala Val
 145
```

( 2 ) INFORMATION FOR SEQ ID NO:5:

( i ) SEQUENCE CHARACTERISTICS:
        ( A ) LENGTH: 295 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 788905

( x i ) SEQUENCE DESCRIPTION: SEQ ID NO:5:

```
Met Ser Ser Arg Lys Ser Thr Ala Ser Ser Leu Leu Leu Arg Gln Tyr
 1               5                  10                  15

Arg Glu Leu Thr Asp Pro Lys Lys Ala Ile Pro Ser Phe His Ile Glu
            20                  25                  30

Leu Glu Asp Asp Ser Asn Ile Phe Thr Trp Asn Ile Gly Val Met Val
         35                  40                  45

Leu Asn Glu Asp Ser Ile Tyr His Gly Gly Phe Phe Lys Ala Gln Met
     50                  55                  60

Arg Phe Pro Glu Asp Phe Pro Phe Ser Pro Pro Gln Phe Arg Phe Thr
 65                  70                  75                  80
```

| | | | | | | | | | | | | | |
|---|---|---|---|---|---|---|---|---|---|---|---|---|---|
| Pro | Ala | Ile | Tyr | His 85 | Pro | Asn | Val | Tyr | Arg 90 | Asp | Gly | Arg | Leu Cys 95 Ile |
| Ser | Ile | Leu | His 100 | Gln | Ser | Gly | Asp | Pro 105 | Met | Thr | Asp | Glu | Pro 110 Asp Ala |
| Glu | Thr | Trp 115 | Ser | Pro | Val | Gln | Thr 120 | Val | Glu | Ser | Val | Leu 125 | Ile Ser Ile |
| Val | Ser 130 | Leu | Leu | Glu | Asp | Pro 135 | Asn | Ile | Asn | Ser | Pro 140 | Ala | Asn Val Asp |
| Ala 145 | Ala | Val | Asp | Tyr | Arg 150 | Lys | Asn | Pro | Glu | Gln 155 | Tyr | Lys | Gln Arg Val 160 |
| Lys | Met | Glu | Val | Glu 165 | Arg | Ser | Lys | Gln | Asp 170 | Ile | Pro | Lys | Gly Phe Ile 175 |
| Met | Pro | Thr | Ser 180 | Glu | Ser | Ala | Tyr | Ile 185 | Ser | Gln | Ser | Lys | Leu Asp Glu 190 |
| Pro | Glu | Ser 195 | Asn | Lys | Asp | Met | Ala 200 | Asp | Asn | Phe | Trp | Tyr 205 | Asp Ser Asp |
| Leu | Asp 210 | Asp | Asp | Glu | Asn | Gly 215 | Ser | Val | Ile | Leu | Gln 220 | Asp | Asp Asp Tyr |
| Asp 225 | Asp | Gly | Asn | Asn | His 230 | Ile | Pro | Phe | Glu | Asp 235 | Asp | Asp | Val Tyr Asn 240 |
| Tyr | Asn | Asp | Asn | Asp 245 | Asp | Asp | Asp | Glu | Arg 250 | Ile | Glu | Phe | Glu Asp Asp 255 |
| Asp | Asp | Asp | Asp 260 | Asp | Asp | Ser | Ile | Asp 265 | Asn | Asp | Ser | Val | Met Asp Arg 270 |
| Lys | Gln | Pro 275 | His | Lys | Ala | Glu | Asp 280 | Glu | Ser | Glu | Asp | Val 285 | Glu Asp Val |
| Glu | Arg 290 | Val | Ser | Lys | Lys | Ile 295 | | | | | | | |